United States Patent
Her

(10) Patent No.: US 10,994,117 B2
(45) Date of Patent: May 4, 2021

(54) MULTI-CAP FOR CONNECTING CATHETER

(71) Applicant: SMHERS, Paju-si (KR)

(72) Inventor: Yun-Hee Her, Seoul (KR)

(73) Assignee: SMHERS, Pauju-si (KR)

( * ) Notice: Subject to any disclaimer, the term of this patent is extended or adjusted under 35 U.S.C. 154(b) by 8 days.

(21) Appl. No.: 15/746,510

(22) PCT Filed: Mar. 30, 2016

(86) PCT No.: PCT/KR2016/003271
§ 371 (c)(1),
(2) Date: Jan. 22, 2018

(87) PCT Pub. No.: WO2017/014405
PCT Pub. Date: Jan. 26, 2017

(65) Prior Publication Data
US 2018/0200501 A1    Jul. 19, 2018

(30) Foreign Application Priority Data

Jul. 21, 2015    (KR) ........................ 10-2015-0103081

(51) Int. Cl.
*A61M 39/20* (2006.01)
*A61M 39/12* (2006.01)
(Continued)

(52) U.S. Cl.
CPC ............ *A61M 39/20* (2013.01); *A61M 25/00* (2013.01); *A61M 39/08* (2013.01); *A61M 39/10* (2013.01);
(Continued)

(58) Field of Classification Search
CPC .... A61J 15/0003; A61M 1/008; A61M 39/10; A61M 2039/1077; A61M 2039/1027;
(Continued)

(56) References Cited

U.S. PATENT DOCUMENTS 3,633,586 A * 1/1972 Sheridan ............... A61M 16/04
128/207.15
3,741,217 A * 6/1973 Ciarico ................. A61M 39/20
604/256

(Continued)

FOREIGN PATENT DOCUMENTS

EP    0621053 A1    10/1994
EP    0640358 A1    3/1995
(Continued)

OTHER PUBLICATIONS

Mila International, Inc., Medical Instrumentation for Animals, International 2014 Catalog, pp. 1-44.

*Primary Examiner* — Nathan R Price
*Assistant Examiner* — Courtney B Fredrickson
(74) *Attorney, Agent, or Firm* — Novick, Kim & Lee, PLLC; Jae Youn Kim

(57) ABSTRACT

Provided is a multi-cap for connecting a catheter and the multi-cap includes: a body having an internal hole formed in a longitudinal direction and having an end connected to a catheter; a cover portion disposed on an outer side of the body in the longitudinal direction of the body and spaced from the body such that the catheter is partially inserted between the outer side of the body and the cover portion. Further, a spout is formed at a second end of the body to transmit an injection substance from the outside to the hole and a capping part is connected to a side of the body to selectively close the inlet of the spout.

5 Claims, 11 Drawing Sheets

(51) Int. Cl.
*A61M 25/00* (2006.01)
*A61M 39/10* (2006.01)
*A61M 39/08* (2006.01)
*F16L 55/10* (2006.01)
*A61M 1/00* (2006.01)
*A61J 15/00* (2006.01)

(52) U.S. Cl.
CPC ............. *A61M 39/12* (2013.01); *F16L 55/10* (2013.01); *A61J 15/0003* (2013.01); *A61M 1/008* (2013.01); *A61M 2039/1027* (2013.01); *A61M 2039/1038* (2013.01); *Y10S 285/901* (2013.01); *Y10S 604/905* (2013.01)

(58) Field of Classification Search
CPC ...... A61M 39/20; A61M 25/00; A61M 39/08; A61M 39/12; A61M 2039/1038; F16L 55/10; Y10S 28/901; Y10S 604/905
See application file for complete search history.

(56) References Cited

U.S. PATENT DOCUMENTS

| | | | | |
|---|---|---|---|---|
| 3,768,476 | A | * | 10/1973 | Raitto ................... A61M 31/00 604/326 |
| 4,137,117 | A | | 1/1979 | Jones |
| 4,187,846 | A | * | 2/1980 | Lolachi ................. A61M 39/18 604/411 |
| 4,187,848 | A | * | 2/1980 | Taylor ................... A61M 5/344 604/243 |
| 4,349,024 | A | * | 9/1982 | Ralston, Jr. ........... A61M 39/12 604/403 |
| 4,963,132 | A | * | 10/1990 | Gibson ................. A61M 39/20 285/331 |
| 5,047,021 | A | * | 9/1991 | Utterberg .............. A61M 39/10 285/332 |
| 5,065,783 | A | * | 11/1991 | Ogle, II ............ A61M 39/045 137/614.21 |
| 5,549,583 | A | * | 8/1996 | Sanford ................ A61M 39/10 604/535 |
| 5,776,117 | A | | 7/1998 | Haselhorst et al. |
| 5,951,519 | A | * | 9/1999 | Utterberg .............. A61M 39/20 604/167.01 |
| 2005/0082828 | A1 | * | 4/2005 | Wicks .................... F16L 37/38 285/319 |
| 2010/0176584 | A1 | * | 7/2010 | Ito ......................... A61M 39/10 285/23 |
| 2011/0006515 | A1 | * | 1/2011 | Yanik .................... A61M 39/18 285/239 |
| 2014/0261758 | A1 | * | 9/2014 | Wlodarczyk ..... A61M 5/14566 137/315.01 |
| 2019/0105484 | A1 | * | 4/2019 | Doornbos ........... A61J 15/0026 |

FOREIGN PATENT DOCUMENTS

| | | |
|---|---|---|
| KR | 10-2006-0090160 A | 8/2006 |
| KR | 10-1116873 B1 | 3/2012 |
| KR | 10-1213215 B1 | 12/2012 |
| KR | 10-1367902 B1 | 2/2014 |
| KR | 10-1590769 B1 | 2/2016 |

\* cited by examiner

MULTI-CAP FOR CONNECTING CATHETER

TECHNICAL FIELD

The present invention relates to a catheter and, more particularly, to a multi-cap that is connected to a catheter to close the inlet of the catheter or easily connect the catheter to a syringe.

BACKGROUND ART

A catheter, which is a kind of medical tube, is widely used as a general name for tube-shaped instruments. There are catheters comprised of various materials and having various sizes and shapes for the usages. Such catheters may be used to extract retained substances in a body cavity or in various organs, absorb cleansing perfusate, measure the status of cardiac blood flow or central venous pressure, inject medicines or contrast media into a body, etc.

A Levin tube, which is a kind of catheter, is a medical instrument for reducing pressure by removing gas or water in the stomach, supplying medicine or food, remedying closed or bleeding portions, securing specimens for gastrointestinal tract examination, and performing gastric lavage is inserted into the stomach through a nostril, the nasal cavity, and the gullet or is directly connected to the stomach to be used.

As in FIG. 1, a common Levin tube T has a connector at an end and a syringe is connected to the connector T' of the Levin tube T, so medicine, contrast agents, or food can be injected into the Levin tube T. A cap C is connected to the connector T' of the connector T to selectively close the connector T' to prevent foreign substances from entering into the Levin tube T when the Levin tube T is not used.

However, in the related art, the connector T' of the Levin tube T and the inlets of syringes are different in size, so it was difficult to accurately connect syringes to the Levin tube T. Further, there was a concern that air or the substances in syringes flow into the Levin tube T.

DISCLOSURE

Technical Problem

The present invention has been made in an effort to solve the problems and an object of the present invention is to make it possible to both close a catheter and connect a syringe, using one multi-cap for connecting a catheter.

Another object of the present invention is to apply a multi-cap for connecting a catheter to catheters having various sizes.

Technical Solution

In order to achieve the objects of the present invention, an aspect of the present invention provides a multi-cap for connecting a catheter, the multi-cap including: a body having an internal hole formed in a longitudinal direction and having an end connected to a catheter; a cover portion disposed on an outer side of the body in the longitudinal direction of the body and spaced from the body such that the catheter is partially inserted between the outer side of the body and the cover portion; a spout protruding from a second end of the body to transmit an injection substance from the outside to the hole; and a capping part connected to a side of the body to selectively close the inlet of the spout.

A space defined between the outer side of the body and the cover portion may decrease in width as the space goes toward the spout.

The body may decease in width as the body goes to a lower portion that is connected with the catheter.

A lower end of the body may protrude farther than a lower end of the cover portion.

A plurality of grooves may be formed on the outer side of the body inserted in the catheter and arranged in the longitudinal direction of the body.

At least one projective rib may be formed on an outer side of the cover portion and arranged in a longitudinal direction of the cover portion.

The capping part may include: a cap lid connected to the body; and a closing projection formed at an end of the cap lid to be inserted into the inlet of the spout.

A coupling rib and a coupling groove that correspond each other may be formed on an outer side of the closing projection and an inner side of the spout, respectively.

The body, the cover portion, the spout, and the capping part may be integrally formed and made of rubber or silicon.

The body may have a connecting part for connecting the body to the catheter.

The connecting part may include a guide made of a flexible material and a connecting ring formed at an end of the guide to surround the catheter or a connector of the catheter.

Advantageous Effects

The multi-cap for connecting a catheter according to the present invention has the following effects.

The multi-cap for connecting a catheter closes the inlet of a catheter and allows an injection instrument such as a syringe and a catheter to be more easily coupled, so work becomes more convenient.

Further, the flexible spout of the multi-cap for connecting a catheter can correspond to syringes (injection instruments) having various sizes, so it is possible to prevent an external substance from flowing outside when injecting the substance.

Further, since the coupling space between the body and the cover portion that constitute the multi-cap for connecting a catheter of the present invention increases in width as it goes down toward the catheter, an insertion force is small at the early stage of connecting the catheter to the multi-cap for connecting a catheter, and when the catheter and the multi-cap for connecting a catheter are completely combined, they can be maintained in a strongly combined state, so convenience in assemblage and stability both can also be improved.

MODE FOR INVENTION

Figure 1:
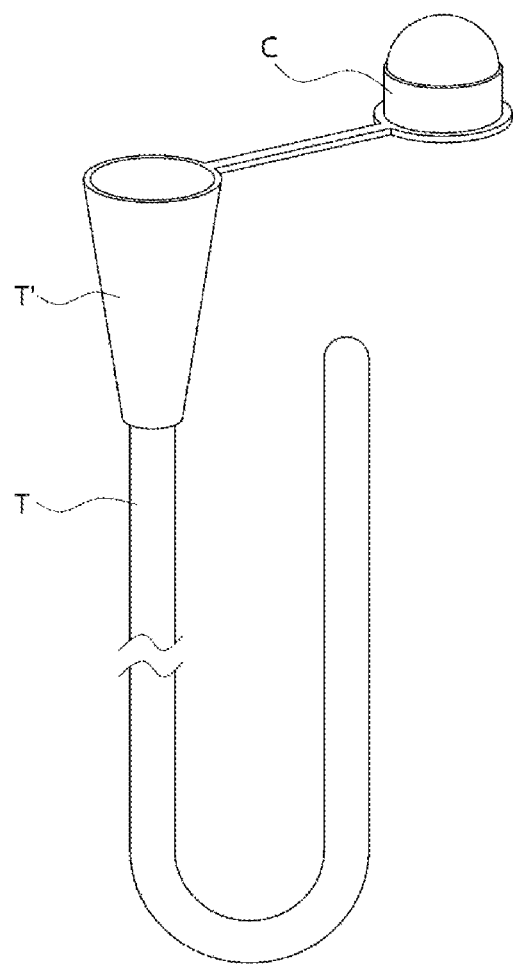
FIG. 1 is a perspective view showing the configuration of a common Levin tube.

Hereinafter, embodiments of the present invention will be described in detail with reference to drawings. When components are given reference numerals in the drawings, the same components are given the same reference numerals even if they are shown in different drawings. Further, in the following description of embodiments of the present invention, when detailed description of well-known configurations or functions is determined as interfering with understanding of the embodiments of the present invention, they are not described in detail.

Further, terms 'first', 'second', 'A', 'B', '(a)', and '(b)' can be used in the following description of embodiments of the present invention. These terms are provided only for discriminating components from other components and, the essence, sequence, or order of the components are not limited by the terms. When a component is described as being "connected", "combined", or "coupled" with another component, it should be understood that the component may be connected or coupled to another component directly or with another component interposing therebetween.

A catheter T is described first for the convenience of description. The catheter T, which is a kind of medical tube, is made of a flexible material and has a connector 10 coupled to an end thereof. The connector 10 is a tapered part to which a syringe 70 is coupled. A Levin tube is exemplified as the catheter T in the following description of an embodiment.

Figure 2:
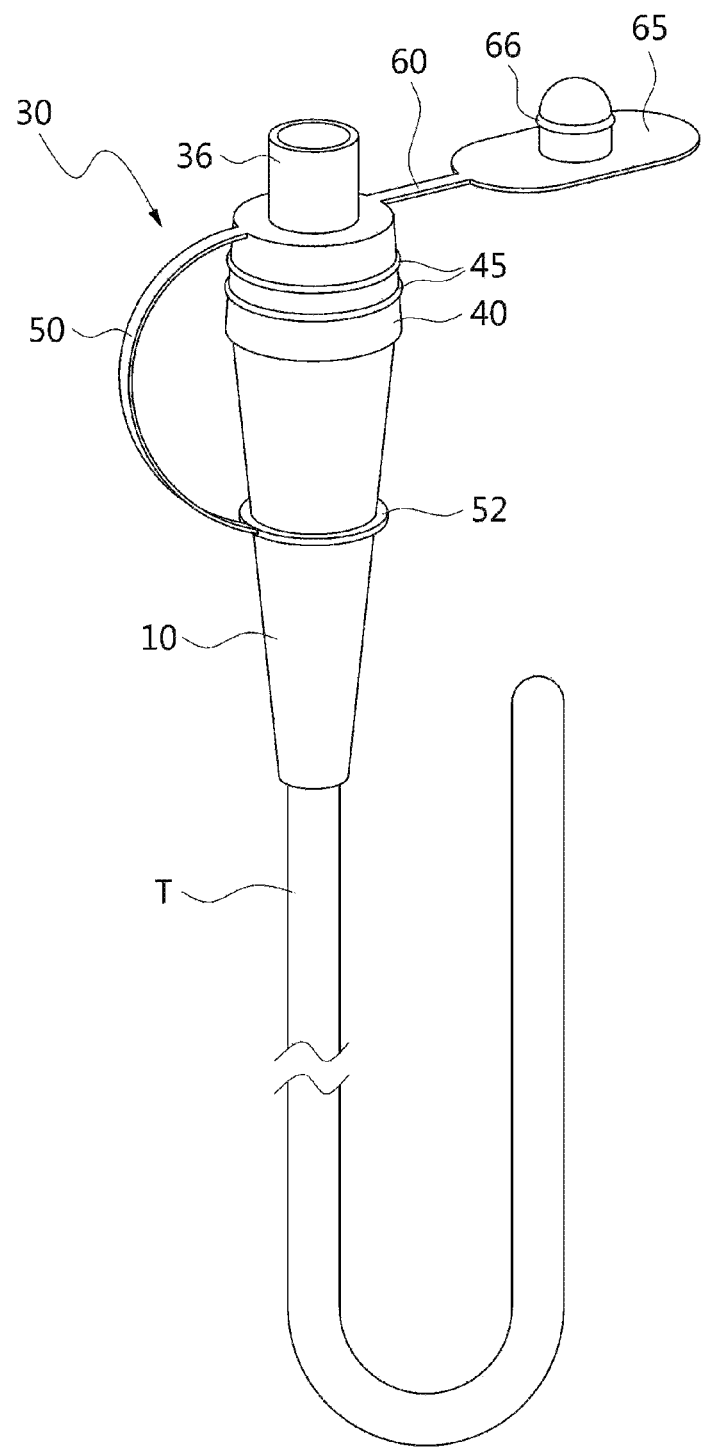
FIG. 2 is a perspective view showing that an embodiment of a multi-cap for connecting a catheter according to the present invention has been applied to a catheter.

According to the present invention, the syringe 70 is not directly connected to the connector 10, and the syringe 70 and the catheter T are indirectly connected to each other through a multi-cap 30 for connecting a catheter. That is, as shown in FIG. 2, the multi-cap 30 for connecting a catheter is coupled to a side of the connector 10 of the catheter T. The multi-cap 30 for connecting a catheter is coupled to the connector 10 of the catheter T and then an injecting instrument that can inject external substances such as the syringe 70 is connected to the cap so that external substances such as nutrients or food can be injected into the catheter T.

The multi-cap 30 for connecting a catheter is made of an elastic material, for example, it may be made of rubber, silicon, or soft plastic. This is for enabling the multi-cap 30 for connecting a catheter to somewhat expand when it is coupled to the catheter T and to return to the initial shape after being separated. In the embodiment, the multi-cap 30 for connecting a catheter is made of silicon and, a body 31, a cover portion 40, a spout 36, and a capping part 60, 66 to be described below are integrally formed.

Figure 3:
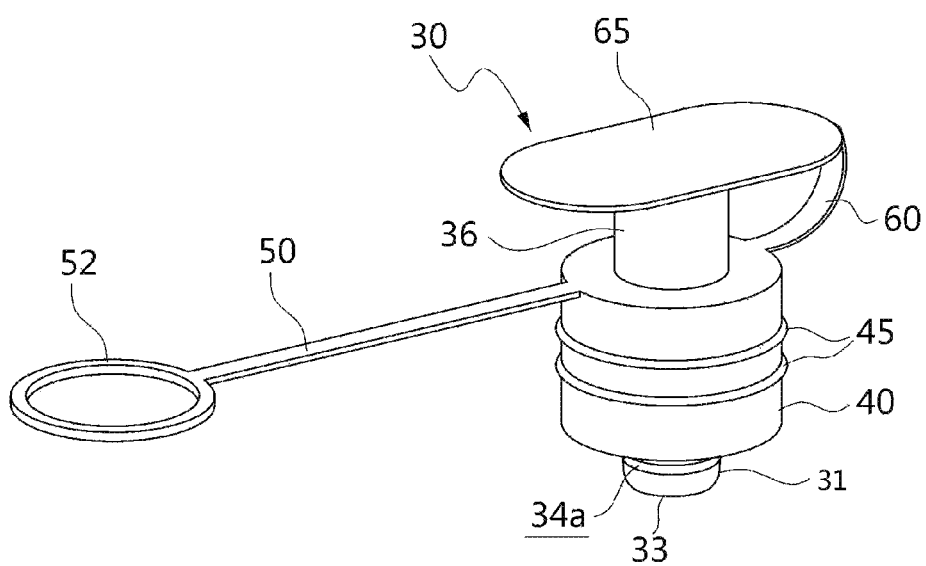
FIG. 3 is a perspective view showing the configuration of the multi-cap for connecting a catheter according to the present invention.
Figure 4:
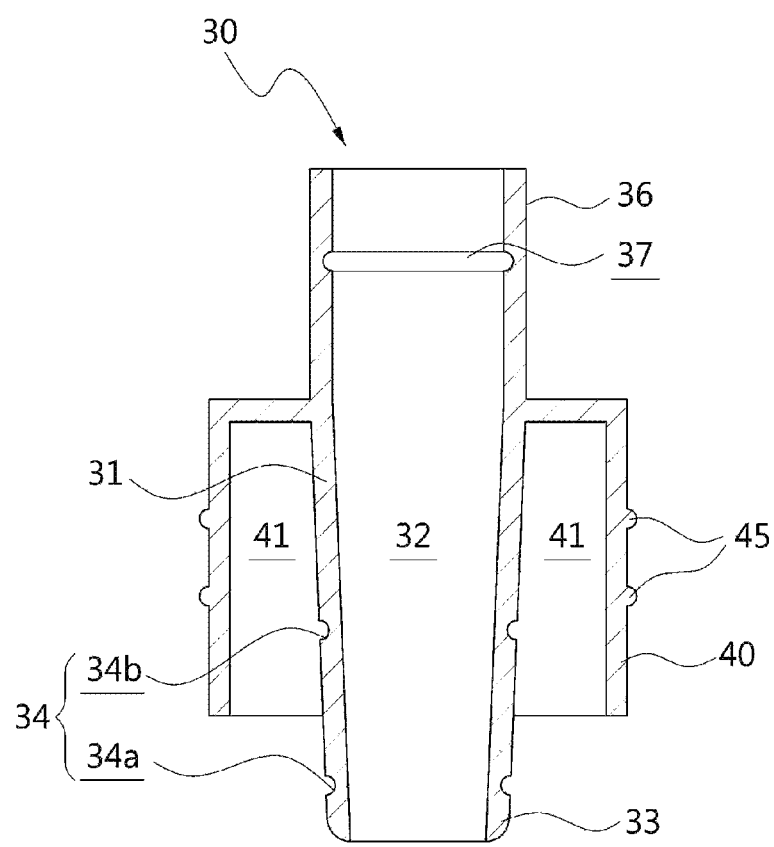
FIG. 4 is a cross-sectional view showing the configuration of the embodiment shown in FIG. 3.

As shown in FIG. 3, the multi-cap 30 for connecting a catheter has the body 31. The body 31 forms the frame of the multi-cap 30 for connecting a catheter and has a substantially cylindrical shape extending upward. Referring to FIG. 4, a hole 32 is formed through the body 31. The hole 32 is an empty space formed in the longitudinal direction of the body 31 and is a part through which an injection substance flows.

The catheter T is connected to the lower end of the body 31. More exactly, the lower end of the body 31 is inserted into the catheter T and a cover portion 40 to be described below covers the outer side of the catheter T.

As shown in FIG. 4, the body 31 decreases in width as it goes down. Accordingly, a coupling space 41 between the body 31 and the cover portion 40 is increased in width as it goes down and is decreased in width as it goes up. Accordingly, the catheter T can be easily inserted into the coupling space 41 in the early stage of coupling the catheter T and the multi-cap 30 for connecting a catheter to each other, and as the multi-cap 30 for connecting a catheter keeps being inserted into the catheter T, the fastening force is gradually increased, thereby strongly coupling the catheter and the cap.

The lower end of the body 31 may protrude downward farther than the lower end of the cover portion 40. This is for easily inserting the lower end of the body 31 into the inlet of the catheter T in the early stage of coupling, by protruding the body 31.

A groove 34 is formed on the outer side of the body 31 that is inserted into the catheter T. The groove 34 is formed around the outer side of the body 31 to reduce an insertion force by decreasing the contact area between the outer side of the body 31 and the inner side of the catheter T when the lower portion of the body 31 is inserted into the catheter T. In the embodiment, the groove 34 is composed of two grooves 34a and 34b formed in the longitudinal direction of the body 31, but the present invention is not limited thereto and one or three or more grooves may be formed.

The spout 36 is formed at the upper portion of the body 31. The spout 36 is a part protruding upward from the body 31, so it may be considered as a portion of the body 31. The spout 36 is coupled to the syringe 70, thereby transmitting an injection substance to the hole 32.

A coupling groove 37 is formed around the inner side of the spout 36. The coupling groove 37 corresponds to a coupling rib 66 formed on a closing projection 65 of the capping part 60, 66, and when the coupling rib 66 is inserted in the coupling groove 37, the capping part 60, 66 and the spout 36 are more strongly combined.

The cover portion 40 is formed on the outer side of the body 31. The cover portion 40 protrudes from the body 31 and extends in the longitudinal direction of the body 31, so when the multi-cap 30 for connecting a catheter is coupled to the catheter T, the cover portion 40 covers the outer side of the catheter T such that the catheter T is positioned between the body 31 and the cover portion 40.

The cover portion 40 is formed in the longitudinal direction of the body 31 and spaced from the outer side of the body 31 such that the coupling space 41 is defined between the outer side of the body 31 and the cover portion 40, so the catheter T is partially inserted into the coupling space 41. Since the body 41 decreases in width as it goes down, the coupling space 41 increases in width as it goes down.

The projective ribs 45 are formed on the outer side of the cover portion 40. One or more projective ribs 45 are arranged in the longitudinal direction of the cover portion 40 and they increase durability of the cover portion 40. Since the cover portion 40 elastically expands when it is coupled to the catheter T, the projective ribs 45 are formed to prevent tearing or plastic deformation of the cover portion 40 in this process.

Figure 5:
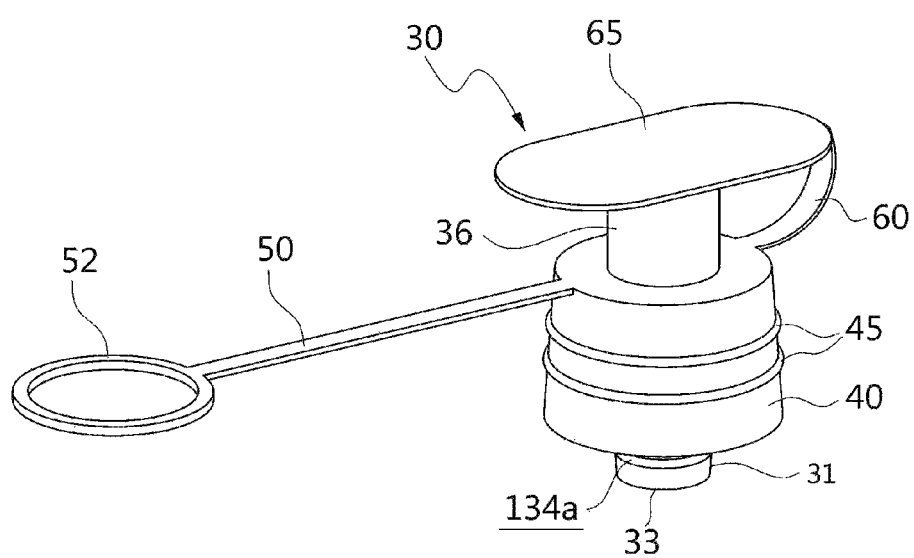
FIG. 5 is a cross-sectional view showing the configuration of another embodiment of a multi-cap for connecting a catheter according to the present invention.
Figure 6:
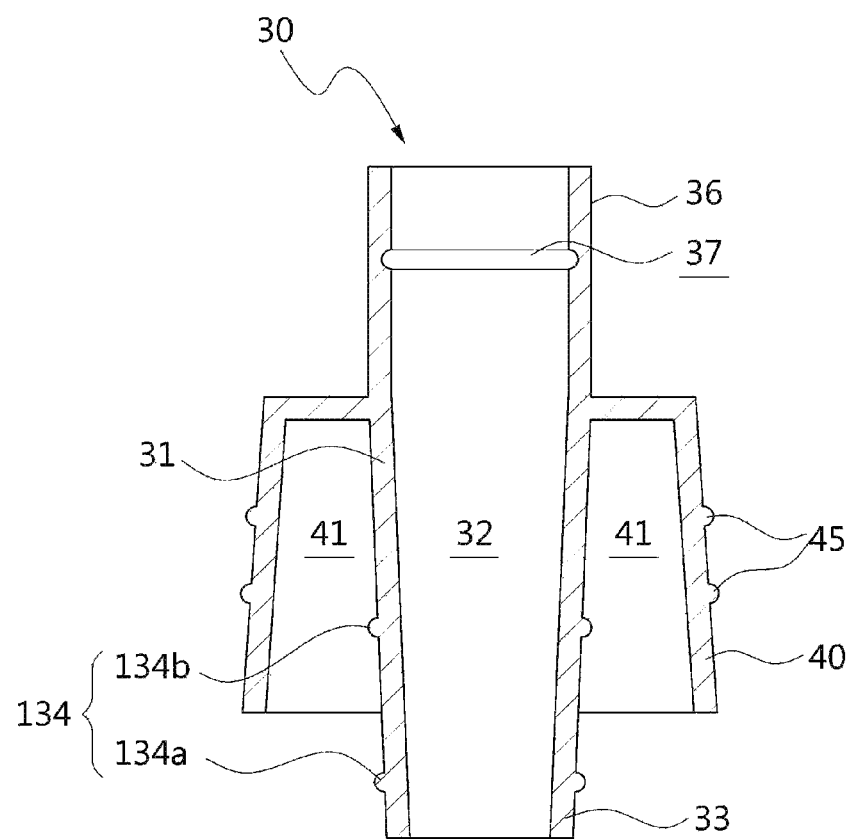
FIG. 6 is a cross-sectional view showing the configuration of the embodiment shown in FIG. 5.

Another embodiment of a multi-cap for connecting a catheter according to the present invention is shown in FIGS. 5 and 6. Differences from the embodiment described above are described hereafter. First, the cover portion 40 of the multi-cap 30 for connecting a catheter may increase in width as it goes down. That is, the cover portion 40 increases in width as it goes down and the body 31 decreases in width as it goes down, so the coupling space 41 increases in width as it goes down to the lower portion of the multi-cap 30 for connecting a catheter and decreases in width as it goes up. Accordingly, the early insertion force of the catheter T and the cap is small, but the coupling force is gradually increased, so after they are completely combined, they can be maintained in a firmly combined state.

Further, a projection 134 instead of the groove 34 may be formed on the body 31. The projection 134 further increases the coupling force between the catheter T and the body 31 by pressing the inner side of the catheter T when the body 31 is inserted in the catheter T.

On the other hand, as shown in FIG. 2, the body 31 has a connecting part 50, 52 that connects the body 31 to the catheter T. The connecting part 50, 52 allows the multi-cap 30 for connecting a catheter to be used while being connected to the catheter T, so even if the multi-cap 30 for connecting a catheter is separated from the catheter T, the connecting portions keep the connected state, whereby it is possible to more safely keep the multi-cap 30 for connecting a catheter without a concern of loss.

The connecting part 50, 52 is composed of a guide 50 made of a flexible material and a connecting ring 52 formed at an end of the guide 50 and surrounding the catheter T or the connector 10 of the catheter T. Since the connecting ring 52 is also made of a flexible material, it can be coupled to the connector 10 or the catheter T that is larger in inner diameter or outer diameter.

The body 31 has a capping part 60, 66. The capping part 60, 66 is formed on a side of the body 31 to selectively close the inlet of the spout 36 and prevents foreign substances from entering into the multi-cap 30 for connecting a catheter by closing the spout 36 of the multi-cap 30 for connecting a catheter when the syringe 70 is not connected to the spout 36.

The capping part 60, 66 is composed of a flexible cap lid 60 connected to the body 31 and a closing projection 65 formed at an end of the cap lid 60 to be inserted into the inlet of the spout 36. The closing projection 65, which is actually inserted into the spout 36, is formed in a substantially semispherical shape, as shown in the figures.

A coupling rib 66 is formed on the outer side of the closing projection 65 to be inserted into the coupling groove 37 formed on the inner side of the spout 36.

Figure 7:
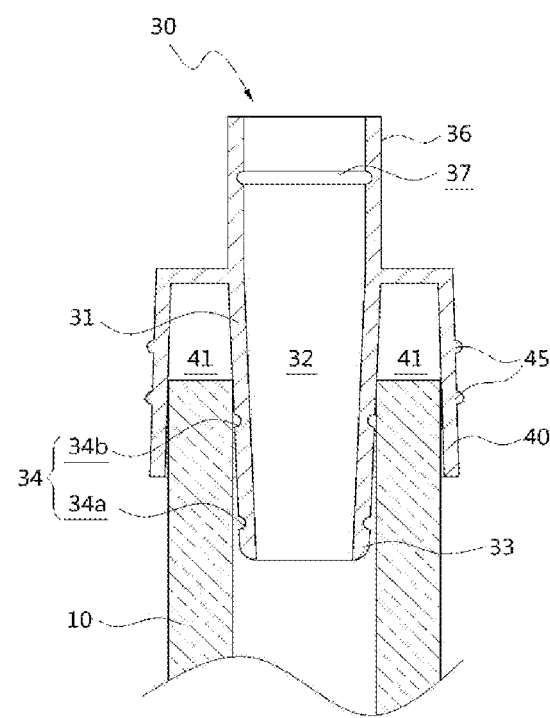
FIGS. 7 and 8 are cross-sectional view sequentially showing a process of coupling a multi-cap for connecting a catheter according to the present invention and a catheter to each other.
Figure 8:
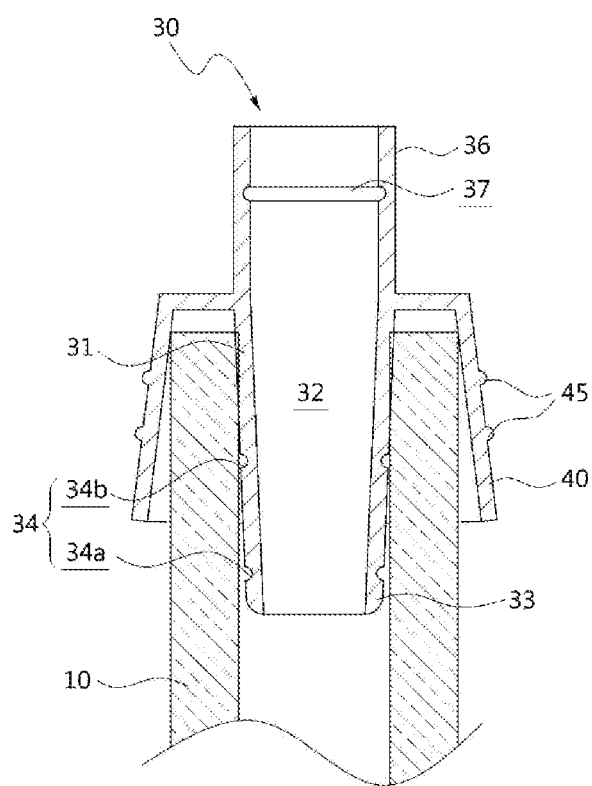

A process of coupling a multi-cap for connecting a catheter according to the present invention and a catheter to each other is described hereafter with reference to FIGS. 7 and 8.

First, the lower portion of the body 31 of the multi-cap 30 for connecting a catheter is inserted into an end of the catheter T, more exactly, the body 31 of the multi-cap 30 for connecting a catheter is inserted into the catheter T and the cover portion 40 covers the outer side of the catheter T.

Since the lower portion of the coupling space 41 between the body 31 and the cover portion 40 is relatively wide, the front end of the catheter T can be easily inserted. This state is shown in FIG. 7.

In this state, when the multi-cap 30 for connecting a catheter is farther inserted into the catheter T, the catheter T is relatively moved upward into the coupling space 41, and in this process, the cover portion 40 is somewhat elastically deformed outward. Further, as shown in FIG. 8, the catheter T keeps firmly coupled between the cover portion 40 and the body 31. Obviously, the degree of coupling of the catheter T and the multi-cap 30 for connecting a catheter may be changed, depending on the thickness or the outer diameter of the catheter T.

Next, a process of connecting a multi-cap for connecting a catheter and a syringe to each other is described with reference to FIGS. 9 to 11.

Figure 9:
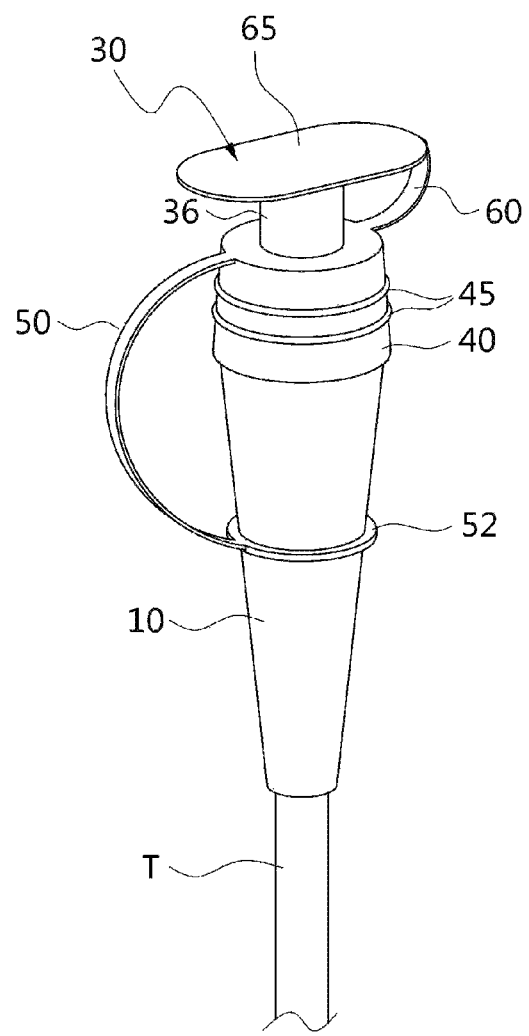
FIGS. 9 to 11 are views sequentially showing a process of connecting a syringe to a catheter, using the present invention.

FIG. 9 shows a coupled state of the multi-cap 30 for connecting a catheter and the catheter T, in which the capping part 60, 66 of the multi-cap 30 for connecting a catheter has closed the spout 36. Accordingly, it is possible to prevent foreign substances from entering into the multi-cap 30 for connecting a catheter and the catheter T before the syringe 70 is coupled.

Figure 10:
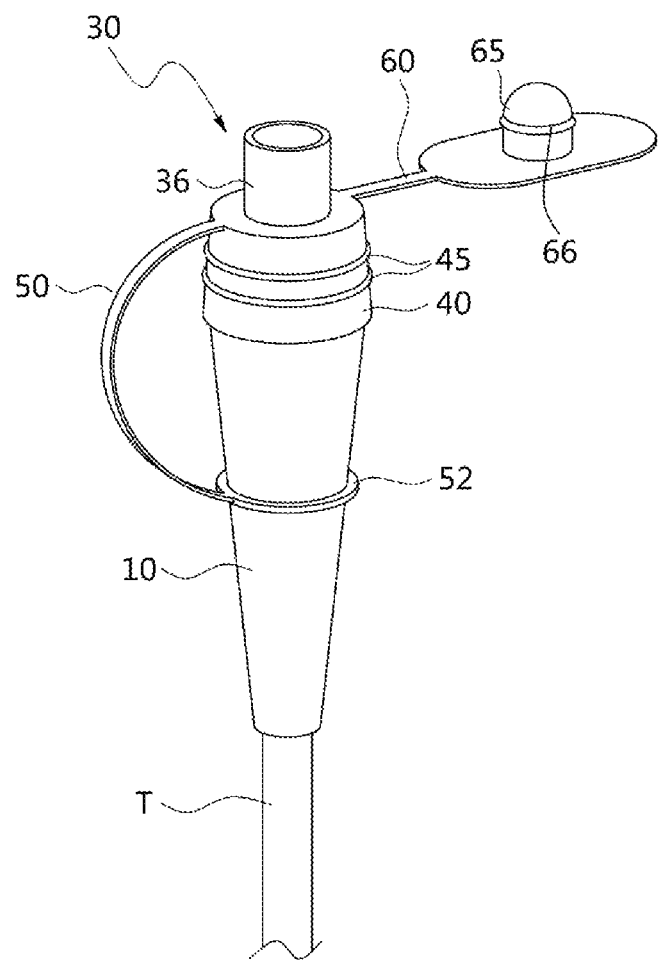
Figure 11:
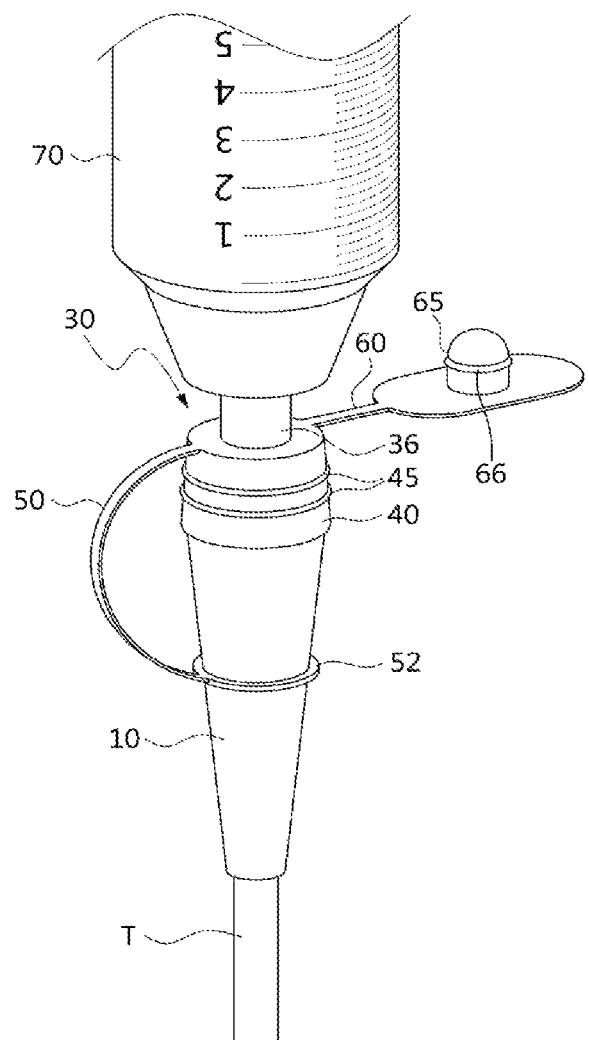

In this state, when the capping part 60, 66 is separated from the spout 36, the spout 36 is opened, as shown in FIG. 10. Further, by inserting the inlet of the syringe 70 into the spout 36, the syringe 70 and the spout 36 can be coupled in close contact with each other, as shown in FIG. 11.

The spout 36 has a size corresponding to the inlet of the syringe 70 and is made of an elastically deformable material, so it is possible to prevent an external substance from flowing outward due to a difference in size between the syringe 70 and the catheter T when injecting the external substance. Obviously, the syringe 70 and the catheter T can be easily coupled to each other by the multi-cap 30 for connecting a catheter.

Even if all components of the embodiments of the present invention were described as being combined in a single unit or operated in combination with each other, the present invention is not limited to the embodiments. That is, one or more of all components may be selectively combined to operate within the scope of the present invention. Further, the terms "comprise", "include", "have", etc. when used in this specification mean that the components can exist unless specifically stated otherwise, so they should be construed as being able to further include other components. Unless otherwise defined, all terms including technical and scientific terms used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The above description merely explains the spirit of the present invention and the present invention may be changed and modified in various ways without departing from the spirit of the present invention by those skilled in the art. Accordingly, the embodiments described herein are provided merely not to limit, but to explain the spirit of the present invention, and the spirit of the present invention is not limited by the embodiments. The patent right of the present invention should be construed by the following claims and the scope and spirit of the invention should be construed as being included in the patent right of the present invention.

The invention claimed is:

1. A multi-cap for connecting a catheter, the multi-cap comprising:
    a body having an internal hole formed in a longitudinal direction and having a lower end configured to be connected to the catheter;
    a cover portion disposed on an outer side of the body in the longitudinal direction of the body and spaced from the body such that the catheter is partially inserted between the outer side of the body and the cover portion;

a spout protruding from an upper end of the body to transmit an injection substance from an outside of the multi-cap to the internal hole; and a capping part connected to a side of the cover portion to selectively close an inlet of the spout, wherein a space defined between the outer side of the body and the cover portion decreases in width as the space goes toward the spout, wherein the body deceases in width as the body goes to the lower end, wherein a plurality of grooves is formed on the outer side of the body and arranged in the longitudinal direction of the body, the plurality of grooves being recessed from an even surface of the outer side of the body and configured to decrease an insertion force when the body is inserted into the catheter, wherein the body, the cover portion, the spout, and the capping part are integrally formed and are made of rubber or silicone, wherein the lower end of the body protrudes farther than a lower end of the cover portion, wherein at least one of the plurality of grooves is formed lower than the lower end of the cover portion, and wherein the at least one of the plurality of grooves is located at a position spaced apart from the lower end of the body, and a cross-sectional shape of the at least one of the plurality of grooves is semicircular.

2. The multi-cap for connecting the catheter of claim 1, wherein at least one projective rib is formed on an outer side of the cover portion.

3. The multi-cap for connecting the catheter of claim 1, wherein the capping part includes:

a cap lid; and a closing projection formed at an end of the cap lid to be inserted into the inlet of the spout.

4. The multi-cap for connecting the catheter of claim 3, wherein a coupling rib and a coupling groove that cooperate with each other are formed on an outer side of the closing projection and an inner side of the spout, respectively.

5. The multi-cap for connecting the catheter of claim 1, further comprising a connecting part connectable to the catheter, and the connecting part includes a guide made of a flexible material and a connecting ring formed at an end of the guide to surround the catheter or a connector of the catheter.

* * * * *